United States Patent [19]
Arnold

[11] Patent Number: 5,893,853
[45] Date of Patent: Apr. 13, 1999

[54] METHOD FOR TRANSPLANTING GRAFTS OF SKIN HAVING AT LEAST ONE HAIR

[76] Inventor: James E. Arnold, 24142 Big Basin Way, Saratoga, Calif. 95070

[21] Appl. No.: 08/789,970

[22] Filed: Jan. 31, 1997

[51] Int. Cl.[6] ................................................ A61B 17/30
[52] U.S. Cl. ...................... 606/133; 606/210; 294/99.2
[58] Field of Search ........................ 606/210, 211, 606/131, 133, 206; 294/99.2; 433/162

[56] References Cited

U.S. PATENT DOCUMENTS

| | | | |
|---|---|---|---|
| 1,521,689 | 1/1925 | King | 294/99.2 |
| 2,943,521 | 7/1960 | Betton | 294/99.2 |
| 3,167,981 | 2/1965 | Kern | 294/99.2 |
| 3,253,327 | 5/1966 | McElligatt | 294/99.2 X |
| 3,638,516 | 2/1972 | Wondowski | 294/99.2 |
| 3,817,078 | 6/1974 | Reed et al. | 294/99.2 X |
| 3,901,243 | 8/1975 | Read | 606/211 X |
| 4,192,204 | 3/1980 | Feldman | 294/99.2 X |
| 4,761,028 | 8/1988 | Duleboln | 606/210 X |
| 4,950,281 | 8/1990 | Kirsch et al. | 294/99.2 X |
| 5,385,471 | 1/1995 | Chuen | 606/210 X |

OTHER PUBLICATIONS

Mueller "The Surgical Armamentarium" p. 715 (1980).

*Primary Examiner*—Michael H. Thaler
*Attorney, Agent, or Firm*—Townsend and Townsend and Crew

[57] ABSTRACT

The invention provides improved forceps and methods. In one exemplary embodiment, a forceps is provided comprising a pair of arms, with each arm having a proximal end and a distal end. The arms are connected near the proximal end, and each arm includes a grasping portion near the distal end. A stop is provided between the arms proximal to the grasping portions to maintain the grasping portions spaced apart from each other.

9 Claims, 2 Drawing Sheets

METHOD FOR TRANSPLANTING GRAFTS OF SKIN HAVING AT LEAST ONE HAIR

BACKGROUND OF THE INVENTION

The invention relates generally to the field of hair transplantation, and more particularly to the placement of grafts of skin having at least one hair into incisions within the scalp. In this regard, the invention provides improved forceps and methods which facilitate the placement of such grafts into the incisions.

Modern hair transplantation procedures typically involve transplanting very small sections of scalp tissue (commonly referred to as grafts) containing between about 1 to 6 hairs. During a single surgical session, the number of transplanted grafts may range from about 300 to about 3,000 or more. In the procedure, the grafts must be moved quickly to ensure survival of the living hairs and to complete the surgery in a timely way.

The grafts are placed in small openings in the portion of the scalp receiving the hairs. To minimize damage to the receiving scalp, the openings for the grafts are made as small as possible, i.e. usually comprising linear incisions measuring about 1 to about 1.5 mm in length or small round holes measuring between about 1 and about 1.5 mm in diameter. To insert the grafts into such small openings, fine tipped stainless steel forceps are used. The forceps grasp the graft and deliberately insert the graft into the opening. The insertion process is challenging since both the graft and the tips of the forceps must be introduced into the opening. Preferably, the forceps introduce the graft at least 4 to 5 mm deep into the scalp. With the graft inserted, the forceps are withdrawn, leaving the graft in place.

During the insertion process, certain risks of damaging the living hairs are present. For example, the forceps, by pressure or by mechanical grinding together of the steel forceps tips, can crush, partially cut or even completely sever hairs in the grafts. Damage to hairs in this manner usually results in poor or no survival of the transplanted hairs. Typical prior art designs of forceps for small graft insertion are generally about 4 to 6 inches in overall length and are commonly referred to as fine tipped forceps. The tips of such forceps have a contact area that measures approximately 0.025 inches in width and about 0.040 inch to about 0.60 inch in length. The contact area used to grasp the grafts is therefore a minimum of about 0.001 square inch. The finger pressure typically applied to the forceps to grasp the graft is approximately 1.0 oz. Such a force applied to a contact area of 0.001 square inch produces a pressure exceeding 62 lb./sq. inch.

Small grafts of approximately 1 to 2 hairs are generally grasped at a lateral edge by the connective tissue along side the individual hairs. If a portion of the hair itself is accidentally grasped, the large force is sufficient to permanently destroy the hair. Larger grafts of about 3 to 6 hairs are grasped with the forceps tips straddling the grafts. There is generally enough resiliency in the larger grafts to tolerate the pressure during insertion of the grafts. However, many grafts may not be sized properly to allow easy insertion. When a graft resists entering the scalp opening, additional pressure may unconsciously or inadvertently be applied to the graft to help quickly place the graft into the incision. In such cases, the finger pressure may be increased to 5.0 oz. or more, creating pressures on the graft tissue of about 312 lbs./sq. inch or more. Such pressures can crush the entire population of hairs within the graft. Many of the hairs are thus in jeopardy of survival with this greater pressure. The pressure is also great enough to allow the forceps to shift from their parallel alignment. As the forceps tips shift there can be a grinding or shearing effect on the graft. This shearing effect can be easily observed as the hairs are severed.

Hence, it would be desirable to provide improved forceps and methods which would limit the pressure applied to hair transplant grafts and to help prevent the grinding together or shearing effect of the forceps tips. In this manner, large numbers of grafts may be rapidly transplanted into small incisions in the scalp without supplying excessive pressure which could otherwise damage or ruin the hairs within the graft.

SUMMARY OF THE INVENTION

The invention provides improved forceps and methods for transplanting grafts of skin having at least one hair into the scalp. In one exemplary embodiment, a forceps is provided which comprises a pair of arms, each of which has a proximal end and a distal end. The arms are connected near the proximal ends, and each arm further includes a grasping portion near the distal end. A stop is provided between the arms proximal to the grasping portions to maintain the grasping portions spaced apart from each other. In this way, regardless of the pressure applied by the surgeon, the amount of pressure applied to the graft by the grasping portions will be limited. Further, since the grasping portions will remain spaced apart, the possibility of having the graft sheared apart by the forceps will be eliminated. Preferably, the stop will maintain the grasping portions spaced apart by a distance of at least 0.1 mm to about 4 mm, and more preferably by about 0.1 mm to about 1 mm.

In one exemplary aspect, the stop is a fixed member, such as a block, which is attached to one of the arms proximal to the grasping portions. As the forceps are squeezed, the block will keep the grasping portions apart. In another aspect, the stop comprises a bend in each of the arms such that the arms are in contact with each other proximal to the grasping portions. As the arms are squeezed, the point of contact between the arms moves proximally to move the grasping portions away from each other.

In a further aspect, the stop is adjustable. In this manner, the distance between the tips may be controlled to accommodate a range of graft sizes. The adjustable stop also allows the control of pressure supplied to the grasping portions so that they will stay within a safe range of pressure. In a preferable aspect, the adjustable stop comprises a threaded pin which extends through at least one of the arms. In this way, the pin may be turned to adjust the length of the stop. In still a further aspect, the arms are constructed out of a flexible material so that when the arms are squeezed to engage the stop, the grasping portions will tend to move away from each other.

The invention further provides an exemplary method for transplanting grafts of skin having at least one hair. According to the method, a forceps is provided comprising a pair of arms which each include a grasping portion near their distal ends. A stop is provided between the arms proximal to the grasping portions to maintain the grasping portions spaced apart from each other. With this configuration, the grasping portions are positioned over at least a portion of a graft of skin having at least one hair. The arms are squeezed to grasp the graft within the grasping portions. The graft is then placed into an incision in the scalp.

To release the graft from the forceps, the user may cease squeezing of the arms or may alternatively squeeze with additional pressure to move the grafting portions away from each other. Preferably the stop will maintain the grasping portions spaced apart by a distance of at least 0.1 mm to about 4 mm, and more preferably by about 0.1 mm to about 1 mm. This distance may be varied by providing an adjustable stop. In an exemplary aspect, the adjustable stop comprises a threaded pin which extends through at least one of the arms. The pin is turned to adjust the spaced apart distance.

In another aspect, the stop comprises at least one block member which is attached to one of the arms proximal to the grasping portions. Alternatively, the stop may comprise a bend in each of the arms such that the arms are in contact with each other proximal to the grasping portion. When the arms are squeezed, the point of contact between the arms moves proximally to move the grasping portions away from each other. In this manner, the graft may be positioned between the grasping portions and the pressure ceased to allow the grasping portions to move toward each other to grasp the graft.

DETAILED DESCRIPTION OF THE SPECIFIC EMBODIMENTS

The invention provides various embodiments of improved forceps and methods which are useful in hair transplantation procedures such as those described in U.S. Pat. No. 5,578,054 and in copending U.S. patent application Ser. Nos. 08/375,312, filed Jan. 18, 1995, now U.S. Pat. No. 5,611,810 08/618,629, filed Mar. 19, 1996, now abandoned 08/375,314, filed Jan. 18, 1995, now U.S. Pat. No. 5,693,064 and 08/375,313, filed Jan. 18, 1995, now abandoned the complete disclosures of which are herein incorporated by reference. The forceps and methods are particularly useful when transplanting large numbers of grafts containing between about 1 to about 6 hairs into the scalp. The number of grafts transplanted by the forceps of the invention may range from about 300 to 3,000 or more in a single operation. The grafts will preferably be placed within small incisions within the scalp which may measure from about 1 mm to about 1.5 mm in length or between about 1 mm and about 1.5 mm in diameter. The forceps will preferably introduce the graft at least 4 or 5 mm deep into the scalp.

Figure 1:
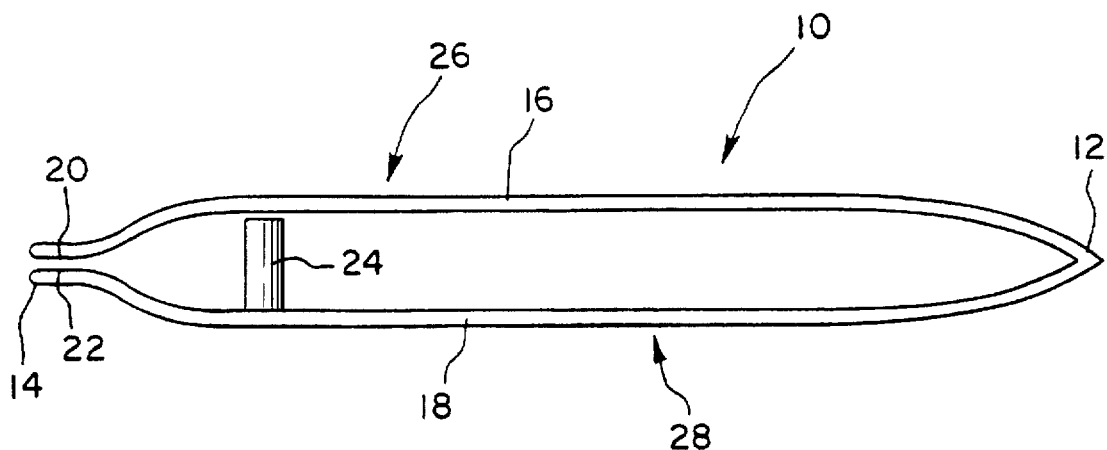
FIG. 1 is a side view of an exemplary embodiment of a forceps having a fixed stop according to the invention.

Referring now to FIG. 1, an exemplary embodiment of a forceps 10 having a proximal end 12 and a distal end 14 will be described. Forceps 10 comprises a pair of arms 16, 18 which are connected at proximal end 12. Each of the arms includes a grasping portion 20, 22 near distal end 14. Proximal to grasping portions 20, 22 is a stop 24 which is attached to arm 18, it being appreciated that stop 24 could also be attached to arm 16.

Stop 24 has a length which is configured to maintain grasping portions 20, 22 spaced apart by a preferred distance when arms 16, 18 are squeezed together. Preferably grasping portions 20, 22 will be maintained spaced apart by at least 0.1 mm to about 0.5 mm when grasping grafts of skin having about 1 to 2 hairs and at least about 0.2 mm to about 1.0 mm when grasping grafts of skin having about 3 to 10 hairs.

Forceps 10 includes a gripping portion 26 and a flexible portion 28. Gripping portion 26 is located just proximal of stop 24 while flexible portion 28 is proximal to gripping portion 26. Arms 16, 18 are preferably constructed of a resilient material, such as stainless steel, which allow the arms to be squeezed together when grasped by gripping portion 26. With this configuration, as a user squeezes gripping portion 26, grasping portions 20, 22 will begin to approach each other until stop 24 engages arm 16. At this point, grasping portions 20, 22 will remain spaced apart even if additional pressure is supplied to gripping portion 26. As additional pressure is supplied, flexible portion 28 will begin to bow inwardly (with stop 24 acting as a fulcrum) to cause grasping portions 20, 22 to move away from each other. In this manner, additional pressure may be supplied to release a graft between grasping portions 20, 22 or may serve as a flag indicating to the surgeon that excessive pressure is being supplied to gripping portion 26.

For most applications, forceps 10 will have a length in the range from about 10 cm to about 20 cm, and grasping portions 20, 22 will each have a surface area of about 0.00005 in$^2$ to about 0.05 in$^2$.

Figure 2:
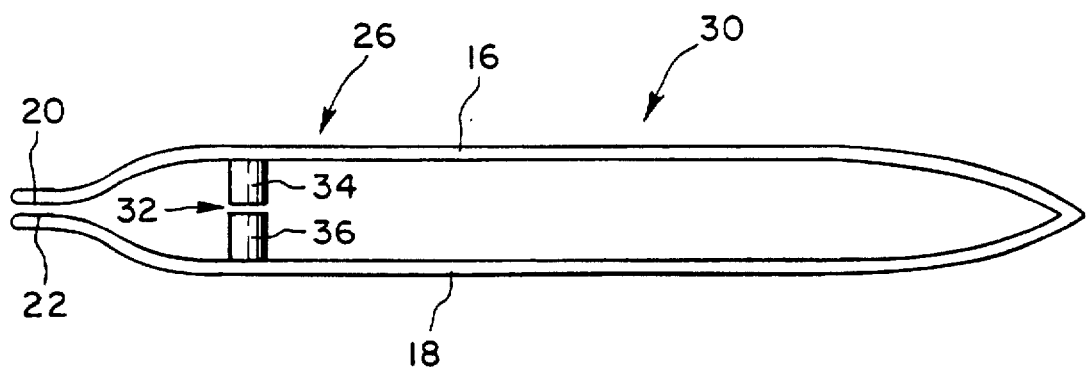
FIG. 2 is a side view of an alternative embodiment of a forceps having an alternative fixed stop according to the invention.

Referring to FIG. 2, an alternative embodiment of a forceps 30 will be described. Forceps 30 is essentially identical to forceps 10 of FIG. 1 except for the configuration of a stop 32. For convenience of discussion, all other elements will be identical to those described in forceps 10. Stop 32 differs from stop 24 in that stop 32 is divided into a pair of halves 34, 36 which are separately attached to arm 16 and arm 18, respectively. As gripping portion 26 is squeezed, halves 34 and 36 will come into contact with each other to prevent grasping portions 20, 22 from contacting each other in a manner similar to that previously described in connection with FIG. 1.

Figure 3:
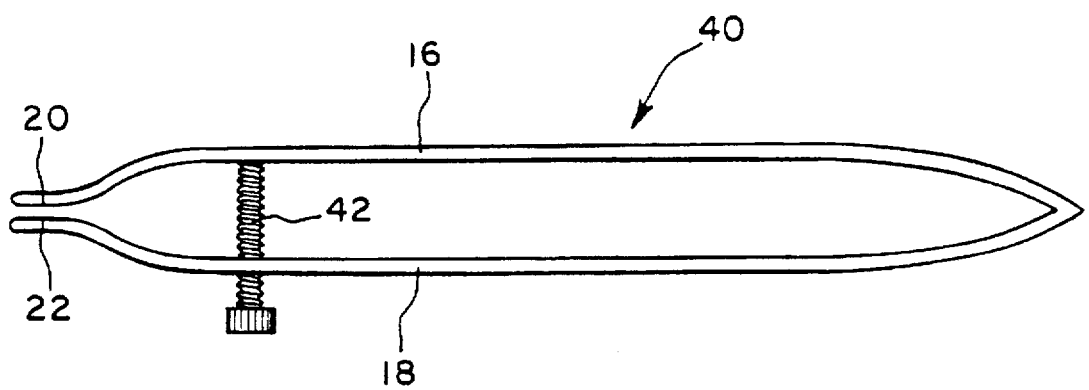
FIG. 3 is a side view of yet another embodiment of a forceps having an adjustable stop.

Referring to FIG. 3, still yet another embodiment of a forceps 40 will be described. Forceps 40 is essentially identical to forceps 10 in FIG. 1 except for the configuration of a stop 42. For convenience of discussion, similar elements as used in FIG. 1 will be used in FIG. 3. Stop 42 comprises a threaded pin which is threaded through a hole (not shown) in arm 18. Stop 42 may be turned to adjust the distance at which grasping portions 20, 22 will be spaced apart when arm 16 engages stop 42. In this manner, stop 42 may be employed to accommodate a wide range of graft sizes. Further, the adjustability of stop 42 allows for the control of the pressure that is applied to grasping portions 20, 22 so that a safe pressure range is maintained when grasping a graft.

Figure 4:
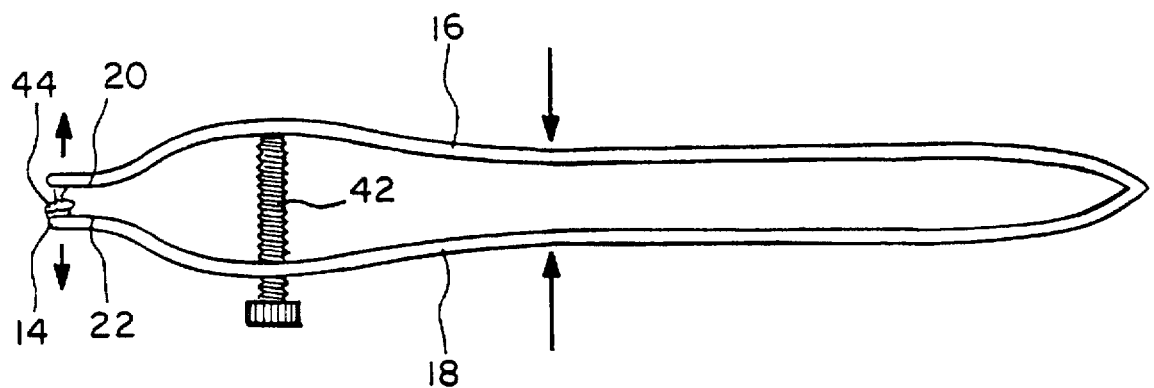
FIG. 4 illustrates the forceps of FIG. 3 when employed to grasp or release a graft according to the invention.

Referring now to FIG. 4, use of forceps 40 to grasp or release a graft 44 will be described. It will be appreciated that a similar method may be employed with the forceps of FIG. 1 and 2. To grasp graft 44, grasping portions 20, 22 are positioned around at least a portion of graft 44 and arms 16, 18 are squeezed together as shown by the arrows. In turn, grasping portions 20, 22 are moved toward each other until they grasp graft 44. As additional pressure is supplied to arms 16, 18 grasping portions 20, 22 will begin to move away from each other as shown by the arrows. This in turn will alert a surgeon that excessive pressure is being supplied to arms 16, 18. With graft 44 securely grasped, forceps 40 are moved to a location on the scalp having an incision and both graft 44 and distal end 14 are inserted into the incision. To release graft 44, the surgeon may cease squeezing arms 16 and 18. Alternatively, the surgeon could supply additional pressure to arms 16, 18 until grasping portions 20, 22 are moved away from each other. The surgeon then grasps additional grafts and places them into other incisions in the scalp.

Figure 5:
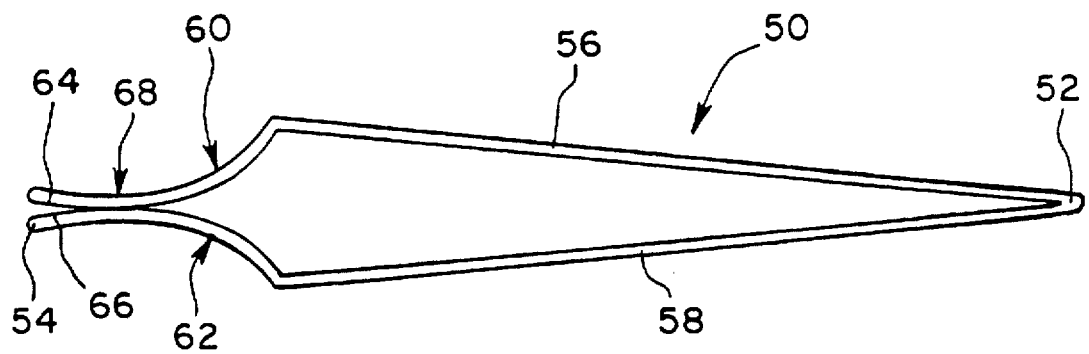
FIG. 5 is a side view of yet another alternative embodiment of a forceps having curved arms which act as a stop according to the invention.
Figure 6:
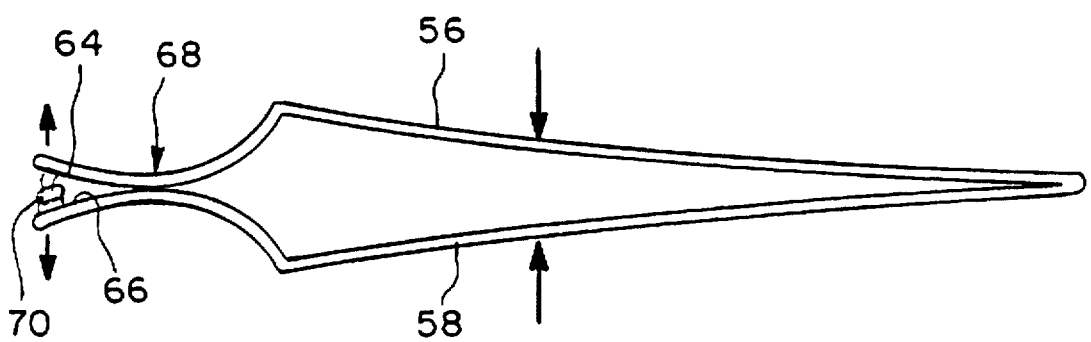
FIG. 6 illustrates the forceps of FIG. 5 when employed to grasp or release a graft.

Referring now to FIG. 5, still yet another embodiment of a forceps 50 will be described. Forceps 50 includes a proximal end 52 and a distal end 54. Forceps 50 comprises a pair of arms 56 and 58 which each include a curved region 60, 62 and grasping portions 64, 66 near distal end 54. Arms 56 and 58 contact each other at a contact point 68 just proximal to grasping portions 64, 66. Arms 56, 58 are constructed of a resilient material so that when squeezed together at a location proximal to curved regions 60, 62 contact point 68 will move proximally as shown in FIG. 6 to further separate grasping portions 64, 66 as shown by the arrows. In this way, a surgeon may grasp a graft 70 by squeezing arms 56, 58 toward each other and then placing grasping portions 64, 66 over a least a portion of graft 70. The squeezing pressure is then ceased to allow contact point 68 to move distally and to allow grasping portions 64, 66 to move closer to each other. It will be understood that grasping portions 64, 66 will not touch each other so that excessive pressure and/or grinding or shearing will not be supplied to graft 70. To release graft 70, arms 56, 58 are squeezed together to move grasping portions 64, 66 away from each other.

The invention has now been described in detail. However, it will be appreciated that certain changes and modifications may be made. Therefore, the scope and content of this invention are not limited by the foregoing description. Rather, the scope and content are to be defined by the following claims.

What is claimed is:

1. A method for transplanting a graft of skin having at least one hair, the method comprising:

providing a forceps comprising a pair of arms, with each arm having a proximal end and a distal end, wherein the arms are connected near the proximal ends, wherein each arm includes a grasping portion near the distal end, wherein a stop is positioned between the arms proximal to the grasping portions to maintain the grasping portions spaced-apart from each other, and wherein the arms each include a gripping portion proximal of the stop and a flexible portion proximal of the gripping portion;

positioning the grasping portions over at least a portion of a graft of skin having at least one hair;

squeezing the arms at the gripping portions to move the grasping portions toward each other and to grasp the graft with the grasping portions, wherein the pressure applied to the graft is limited by the stop, and wherein if excessive forces are applied to the arms during squeezing, the flexible portions will bow inward causing the grasping portions to move away from each other so that the pressure applied to the graft will be limited to prevent damage to the graft;

placing the graft into an incision in the scalp; and squeezing with additional pressure to release the graft from the grasping portions.

2. A method as in claim 1, wherein the stop maintains the grasping portions spaced-apart by a distance of at least about 0.1 mm to about 4 mm.

3. A method as in claim 2, further comprising adjusting the stop to vary the distance by which the grasping portions are spaced-apart.

4. A method as in claim 3, wherein the stop comprises a threaded pin which extends through at least one of the arms, and further comprising turning the pin to adjust the spaced-apart distance.

5. A method as in claim 1, wherein the stop comprises at least one block member which is attached to one of the arms proximal to the grasping portions.

6. A method for transplanting a graft of skin having from 1 to about 10 hairs, the method comprising:

providing a forceps comprising a pair of arms, with each arm having a proximal end and a distal end, wherein the arms are connected near the proximal ends, wherein each arm includes a grasping portion near the distal end, and wherein a stop is provided between the arms proximal to the grasping portions to maintain the grasping portions spaced-apart from each other;

positioning the grasping portions over at least a portion of a graft of skin having from 1 to about 10 hairs;

squeezing the arms to move the grasping portions toward each other and to grasp the graft with the grasping portions, wherein the stop maintains the grasping portions spaced apart by a distance of at least 0.1 mm to about 0.5 mm if the graft has only about 1 to 2 hairs, or if the graft has only at least about 0.2 mm to about 1.0 mm, if the graft has about 3 to 10 hairs, and wherein the pressure applied to the graft is limited by the stop so that the pressure applied to the graft will be limited to prevent damage to the graft;

placing the graft into an incision in the scalp; and squeezing with additional pressure to release the graft from the grasping portions.

7. A method as in claim 6, wherein the stop comprises at least one block member which is attached to one of the arms proximal to the grasping portions.

8. A method as in claim 6, further comprising adjusting the stop to vary the distance by which the grasping portions are spaces-apart.

9. A method as in claim 8, wherein the stop comprises a threaded pin which extends through at least one of the arms, and further comprising turning the pin to adjust the spaced-apart distance.

* * * * *